US012642958B2

(12) United States Patent
Ashby et al.

(10) Patent No.: US 12,642,958 B2
(45) Date of Patent: Jun. 2, 2026

(54) TRANSCUTANEOUS VAGUS NERVE STIMULATION

(71) Applicant: Covidien LP, Mansfield, MA (US)

(72) Inventors: Mark P. Ashby, Laguna Niguel, CA (US); Varun Umesh Kashyap, Palo Alto, CA (US); Scott R. Stanslaski, Shoreview, MN (US); David J. Miller, Austin, TX (US); Erik P. Fahimi, Aliso Viejo, CA (US)

(73) Assignee: Covidien LP, Mansfield, MA (US)

( * ) Notice: Subject to any disclaimer, the term of this patent is extended or adjusted under 35 U.S.C. 154(b) by 295 days.

(21) Appl. No.: 18/469,854

(22) Filed: Sep. 19, 2023

(65) Prior Publication Data

US 2024/0091524 A1      Mar. 21, 2024

Related U.S. Application Data

(60) Provisional application No. 63/478,452, filed on Jan. 4, 2023, provisional application No. 63/376,515, filed on Sep. 21, 2022.

(51) Int. Cl.
A61N 1/04 (2006.01)
A61N 1/36 (2006.01)

(52) U.S. Cl.
CPC ....... A61N 1/0456 (2013.01); A61N 1/36031 (2017.08); A61N 1/36034 (2017.08)

(58) Field of Classification Search
None
See application file for complete search history.

(56) References Cited

U.S. PATENT DOCUMENTS

| | | | |
|---|---|---|---|
| 7,228,167 B2 | 6/2007 | Kara et al. | |
| 7,840,278 B1 | 11/2010 | Puskas | |
| 8,792,989 B2 | 7/2014 | Guntinas-Lichius et al. | |
| 9,254,383 B2 * | 2/2016 | Simon ................ | A61N 1/36034 |
| 10,322,284 B2 | 6/2019 | Lesser et al. | |

(Continued)

FOREIGN PATENT DOCUMENTS

| | | |
|---|---|---|
| JP | 2014018445 A | 2/2014 |
| KR | 20180106382 A | 10/2018 |

(Continued)

OTHER PUBLICATIONS

International Search Report and Written Opinion of International Application No. PCT/US2023/074673 dated Jan. 8, 2024, 14 pp.

(Continued)

*Primary Examiner* — Carl H Layno
*Assistant Examiner* — Bryan McAllister Lee
(74) *Attorney, Agent, or Firm* — Shumaker & Sieffert, P.A.

(57)      ABSTRACT

An example system includes a collar; a first stimulating electrode array positioned on the collar and configured to delivery stimulation therapy to a patient; a second stimulating electrode array being positioned on the collar and configured to deliver stimulation therapy to the patient; a sensor array being positioned on the collar and configured to detect one or more features indicative of laryngeal muscle activity of the patient; and a controller configured to control stimulation therapy to be delivered via the first stimulating electrode array and the second stimulating electrode array.

23 Claims, 6 Drawing Sheets

(56)                References Cited

U.S. PATENT DOCUMENTS

| 10,485,971 | B2 | 11/2019 | Schepis et al. |
| 11,423,760 | B2 | 8/2022 | Nemo et al. |
| 2014/0067021 | A1 | 3/2014 | Rezai et al. |
| 2015/0112238 | A1 | 4/2015 | Cockerill et al. |
| 2017/0095199 | A1 | 4/2017 | Kranck |
| 2021/0220663 | A1 | 7/2021 | Kim |
| 2021/0290943 | A1 | 9/2021 | Hool |
| 2021/0339023 | A1 | 11/2021 | Rangarajan et al. |
| 2021/0402173 | A1 | 12/2021 | Simon et al. |
| 2022/0054864 | A1 | 2/2022 | Baldoni |
| 2022/0118257 | A1 | 4/2022 | Huston et al. |

FOREIGN PATENT DOCUMENTS

| WO | 2021026606 | A1 | 2/2020 |
| WO | 2022061070 | A1 | 3/2022 |

OTHER PUBLICATIONS

Bonaz et al., "Anti-inflammatory properties of the vagus nerve: potential therapeutic implications of vagus nerve stimulation", The Journal of Physiology, vol. 594, No. 20, The Physiological Society, Oct. 15, 2016, pp. 5781-5790, doi: 10.1113/JP271539.

Botzanowski et al., "Noninvasive Stimulation of Peripheral Nerves using Temporally-Interfering Electrical Fields", bioRxiv, Dec. 15, 2021, 13 pp., https://doi.org/10.1101/2021.12.14.472557.

Bremmer et al., "Application of Noninvasive Vagal Nerve Stimulation to Stress-Related Psychiatric Disorders", Journal of Personalized Medicine, vol. 10, No. 119, MDPI, Sep. 9, 2020, 25 pp., doi:10.3390/jpm10030119.

Cai et al., "Vagus nerve stimulation in ischemic stroke: old wine in a new bottle", Frontiers in Neurology, vol. 5, No. 107, PMC, Jun. 24, 2014, 8 pp., doi: 10.3389/fneur.2014.00107.

Gurel et al., "Automatic Detection of Target Engagement in Transcutaneous Cervical Vagal Nerve Stimulation for Traumatic Stress Triggers", IEEE Journal of Biomedical and Health Informatics, vol. 24, No. 7, PMC, Jul. 1, 2021, pp. 1917-1925, doi:10.1109/JBHI.2020.2981116.

Mirzakhalili et al., "Biophysics of Temporal Interference Stimulation", Cell Systems, vol. 11, Elsevier, Dec. 16, 2020, pp. 557-572, https://doi.org/10.1016/j.cels.2020.10.004.

Mravec et al., "The role of the vagus nerve in stroke", Autonomic Neuroscience: Basic and Clinical, vol. 158, Elsevier, Aug. 29, 2010, pp. 8-12, doi:10.1016/j.autneu.2010.08.009.

Omari et al., "The vagal nerve stimulation outcome, and laryngeal effect: Otolaryngologists roles and perspective", American Journal of Otolaryngology—Head and Neck Medicine and Surgery, vol. 38, Elsevier, Jan. 2, 2017, pp. 408-413, doi.org/10.1016/j.amjoto.2017.03.011.

Oshinsky et al., "Non-Invasive Vagus Nerve Stimulation as Treatment for Trigeminal Allodynia", Pain, vol. 155, No. 5, PMC, Feb. 14, 2014, pp. 1037-1042, doi: 10.1016/j.pain.2014.02.009.

Park et al., "Physiological Evaluation of a Non-invasive Wearable Vagus Nerve Stimulation (VNS) Device", Advances in Human Factors in Wearable Technologies and Game Design, vol. 973, Jun. 14, 2019, pp. 57-62, https://doi.org/10.1007/978-3-030-20476-1_7.

Van Der Meij et al., "Non-invasive Vagus nerve stimulation in acute Ischemic Stroke(NOVIS): a study protocol for a randomized clinical trial", Current Controlled Trials in Cardiovascular Medicine, vol. 21, No. 1, Oct. 26, 2020, 6 pp., doi.org/10.1186/s13063-020-04794-1.

Wang et al., "Vagus nerve stimulation in brain diseases: Therapeutic applications and biological mechanisms", Neuroscience and Biobehavioral Reviews, vol. 127, Elsevier, Apr. 18, 2021, pp. 37-53, doi.org/10.1016/j.neubiorev.2021.04.018.

International Preliminary Report on Patentability from International Application No. PCT/US2023/074673 dated Mar. 1, 2025, 9 pp.

* cited by examiner

TRANSCUTANEOUS VAGUS NERVE STIMULATION

This application claims the benefit of U.S. Provisional Application No. 63/478,452 filed 4 Jan. 2023, and U.S. Provisional Application No. 63/376,515 filed 21 Sep. 2022. The entire content of each application is hereby incorporated by reference.

TECHNICAL FIELD

The disclosure relates to devices and techniques for performing transcutaneous vagus nerve stimulation of a patient.

BACKGROUND

Electrical stimulation of the vagus nerve has been shown to be useful for a wide range of purposes. Vagus nerve stimulation (VNS) has been shown to reduce the volume of cerebral infarctions and improve neurological score in numerous animal studies including on rats with cerebral ischemia. Furthermore, VNS also helped in the rehabilitation period post stroke by improving forelimb motor function on rats by almost two times compared to the control group. Along with motor functions, clinical studies have also shown that VNS has been successful in improving sensory function of the forelimb.

Growing evidence suggests that VNS has central and peripheral anti-inflammatory effects on progression of ischemic injury in patients with stroke. These are mediated through both the afferent and efferent pathways of the vagus nerve. The afferent pathway acts by stimulation of locus ceruleus resulting in Hypothalmic-Pituitary-Adrenal (HPA) axis activation and consequent release of cortisol.

SUMMARY

Noninvasive VNS has been shown to downregulate inflammatory cytokines and to reduce infarct growth and/or volume resulting from stroke. However, current techniques for noninvasive VNS leave too much room for therapeutic error that may result in the techniques being therapeutically unreliable. Some current techniques for noninvasive VNS may rely upon manual application of stimulation electrodes over the vagus nerve in the cervical region and/or do not provide feedback regarding the attempted VNS, which may result in ineffective treatment.

In general, the disclosure is directed to devices, systems, and techniques for performing transcutaneous VNS, for example, stimulating one or more vagus nerves via electrodes arranged in collar to be positioned over the left and right cervical vagus nerve when the collar is secured around the patient's neck. The collar may further include an array of sensors to detect one or more parameters that indicate whether one or more vagus nerves are being stimulated and an indicator to indicate to a caregiver whether the vagus nerves are being stimulated. A collar arranged with electrodes and feedback, as described herein, may provide for application by caregivers with reduced skillsets and required training as compared to existing solutions, and may allow someone of relatively lower skill to successfully stimulate the vagus nerve and to do so quickly and effectively. Additionally, bilateral stimulation electrode arrays may provide multiple potential stimulation zones, which may greatly increase the chance of successful stimulation based on initial securement of collar to patient. For example, the collar and associated techniques may facilitate providing VNS quickly that is consistent, effective, and/or user-friendly, such as by an emergency medical technician (EMT) or any other caregiver along the patient's acute and/or chronic care pathway, which would provide great help treating a patient suffering from stoke, TBI, and/or other detrimental conditions driven by inflammation or other disease states benefitting from VNS, and may improve patient outcomes, shorten length of hospital stays, and/or reduce medical costs. In some examples, the collar may obtain feedback via wireless communication with other implantable or wearable devices, such as an implantable cardiac monitor or other cardiac monitoring device or a smartwatch.

In one example, the disclosure is directed to a system comprising a collar; a first stimulating electrode array positioned on the collar and configured to delivery stimulation therapy to a patient; a second stimulating electrode array being positioned on the collar and configured to deliver stimulation therapy to the patient; a sensor array being positioned on the collar and configured to detect one or more features indicative of laryngeal muscle activity of the patient; and a controller configured to control stimulation therapy to be delivered via the first stimulating electrode array and the second stimulating electrode array.

In another example, this disclosure is directed to a method including applying, by a controller, initial stimulation therapy to a patient via one or more of a first stimulating electrode array and a second stimulating electrode array, the first stimulating electrode array and the second stimulating electrode array being positioned on a collar; detecting, by a sensor array, one or more features indicative of laryngeal muscle activity of the patient, the sensory array being positioned on the collar; determining, by the controller, a level of the laryngeal muscle activity based on the one or more features; and determining, by the controller, whether the level of the laryngeal muscle activity is less than a laryngeal muscle activity threshold.

The details of one or more examples are set forth in the accompanying drawings and the description below. Other features, objects, and advantages of the disclosure will be apparent from the description and drawings, and from the claims.

The above summary is not intended to describe each illustrated example or every implementation of the present disclosure.

DETAILED DESCRIPTION

Figure 1:
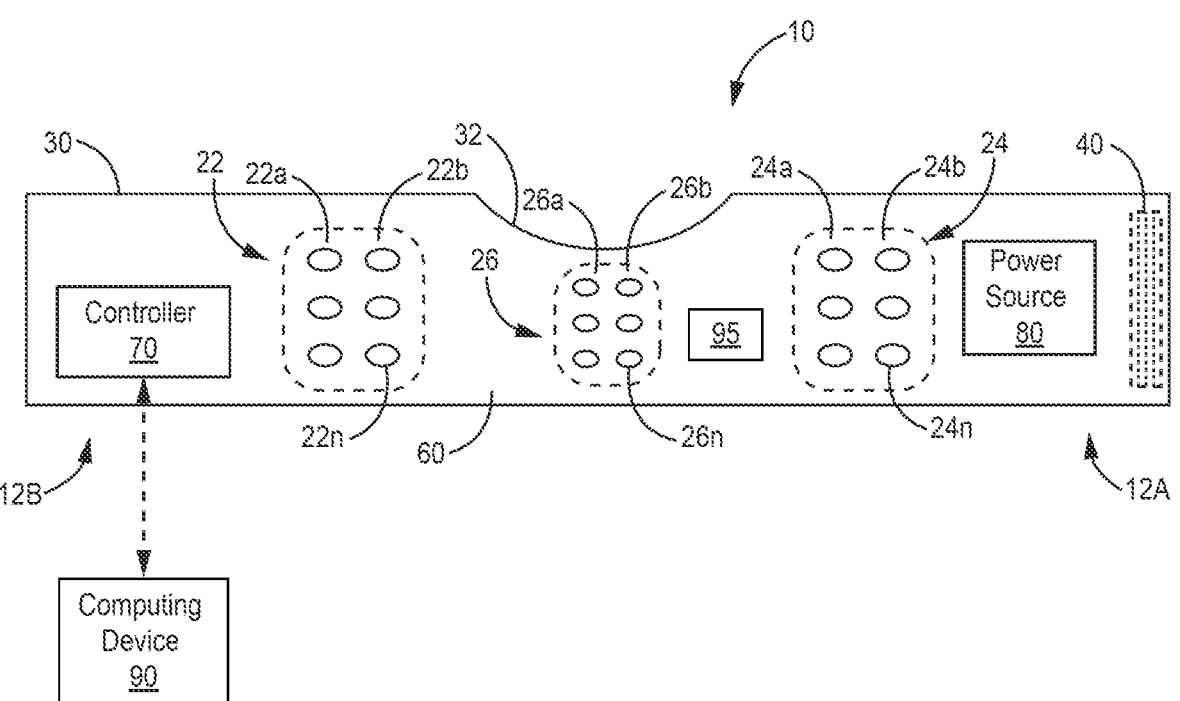
FIG. 1 illustrates a conceptual diagram of an example stimulation device in accordance with one or more techniques of the present disclosure.

Recent discoveries relating to VNS have uncovered the nervous system involvement and control of the body's inflammatory response. The nervous system senses inflammation, pathogens, and tissue damage, as well as modulates the response. Animal and human studies have shown that stimulating the vagus nerve may dampen the inflammatory response and associated cytokines. Recent studies have shown that by varying the stimulation, inflammatory cytokines can be modulated up or down.

In addition, VNS may assist in stroke rehabilitation and treat ischemia reperfusion injury. After a cerebral infarct or stroke, reperfusion therapies (surgery or drugs) are given to restore blood flow. However, due to the ischemia and restoration of blood flow local damage occurs, which is called ischemia reperfusion injury. This will induce local cerebral accumulations of chemical mediators such as reactive oxygen species (ROS) production, inflammatory cytokines, bradykinin, etc. Thus, the inflammatory state is worsened. The inflammatory compounds will trigger sensory signaling, which might lead to a reduced organ vagal activity and sympathetic overdrive. VNS may treat reperfusion damage as the inflammatory state may be lowered by increasing parasympathetic drive.

Noninvasive VNS has been shown to downregulate inflammatory cytokines and more specifically to reduce infarct growth and/or volume resulting from stroke. However, current methods of application leave too much room for therapeutic error as some rely on the manual application of stimulation electrodes (e.g., pad or patch electrodes) over the vagus nerve in the cervical region and/or do not provide feedback to confirm vagus stimulation. Some current methods of application of noninvasive VNS may not properly direct VNS therapy, which may be based, in part, on the lack of feedback. Additionally, therapeutic regimens may require periodic applications of stimulation energy at multiple, predetermined time intervals, potentially requiring reapplication of electrodes each time. The combination of these conditions may lead to inconsistent therapy application and suboptimal results. A VNS device eliminating these potential inconsistencies would provide great benefit for patients suffering stroke, traumatic brain injury (TBI), and other detrimental conditions driven by inflammation.

In general, the disclosure is directed to devices, systems, and techniques for performing transcutaneous VNS that may reduce or eliminate inconsistent VNS therapy being applied by current noninvasive VNS, which would provide great benefit for patients suffering stroke, traumatic brain injury (TBI), and/or other detrimental conditions driven by inflammation or other conditions benefitting from VNS.

While the examples described herein are related to acute therapies for stroke and TBI, the stimulation device 10 may be utilized to deliver numerous other acute and chronic therapies known to respond to VNS. These include, but are not limited to: ischemic stroke/reperfusion injury; TBI; hemorrhagic stroke; epilepsy; obstructive sleep apnea (OSA); heart failure (HF); myocardial infarction (MI); heart rhythm issues; Sepsis; Post-operative ileus; Acute kidney injury; stroke rehabilitation; autoimmune; depression; Anxiety; post-traumatic stress disorder (PTSD); Parkinson's disease PD; Autonomic Dysrelxia (AD); Autism spectrum disorder (ASD); Cognitive disorder (CD).

FIG. 1 is a conceptual diagram illustrating an example stimulation device 10. Stimulation device 10 may provide stimulation to a nerve, such as the vagus nerve. In some examples, stimulation device 10 may provide the stimulation noninvasively. In some examples, stimulation device 10 may be configured to provide unilateral, bilateral, or alternating-side stimulation to a left vagus nerve and a right vagus nerve of a patient.

Stimulation device 10 may include first stimulating electrode array 22 and second stimulating electrode array 24.

The first stimulating electrode array 22 may include one or more electrodes 22a, 22b . . . 22n. In some examples, the first stimulating electrode array 22 may have six electrodes, as shown in FIG. 1, but may also have more or less electrodes, such as, but not limited to, 2, 4, 8, 10, 12. In some examples, each electrode in array 22 may be independent of all other electrodes within the array, and may be operated paired in bipolar fashion to any one or more electrodes within the array 22. The second stimulating electrode array 24 may include one or more electrodes 24a, 24b . . . 24n. In some examples, the second stimulating electrode array 24 may have six electrodes, as shown in FIG. 1, but may also have more or less electrodes, such as, but not limited to, 2, 4, 8, 10, 12. In some examples, each electrode in array 24 may be independent of all other electrodes within the array, and may be operated paired in bipolar fashion to any one or more electrodes within the array 22. First stimulating electrode array 22 may be configured to stimulate a vagus nerve, such as the left or right cervical vagus nerve. Second stimulating electrode array 24 may be configured to stimulate a vagus nerve, such as the left or right cervical vagus nerve, on the opposite side of the neck that the first stimulating electrode array 22.

In some examples, a stimulation waveform may be monophasic or biphasic with amplitudes from 0-25 mA, a pulse width of 20-450 us and rates, such as frequency, of 5-500 Hz. Amplitudes, pulse width, and/or rates may be amounts outside of these ranges as well. In some examples, one or more electrodes in first stimulating electrode array 22 and/or one or more electrodes in second stimulating electrode array 24 may provide a low current alternating current (AC) or direct current (DC) waveform. The low current AC or DC waveform may allow for amplitude and/or periodic adjustments to be made based on feedback loop.

Stimulation device 10 may further include sensor array 26. The sensor array 26 may include one or more sensors 26a, 26b . . . 26n. In some examples, the sensor array 26 may have six sensors, as shown in FIG. 1, but may also have more or less sensors, such as, but not limited to, 2, 4, 8, 10, 12.

Stimulation device 10 may include a collar 30 in which first stimulating electrode array 22, second stimulating electrode array 24, and sensor array 26 are positioned on collar 30. In some examples, first stimulating electrode array 22, second stimulating electrode array 24, and sensor array 26 are arranged on an inner surface 60 of collar 30. A surface of collar 30 that faces the patient while wrapped around the neck of the patient is considered the inner surface 60 of collar 30. The surface opposite the inner surface is considered the outer surface (not shown in FIG. 1). Collar 30 may be configured to be wrapped around a neck of a patient when one or more of first stimulating electrode array 22, second stimulating electrode array 24, or sensor array 26 are in use. Collar 30 may be formed of a variety of materials and have a variety of different sizes and/or thicknesses. Collar 30 may be flexible to fit a variety of sizes of necks. Collar 30 may be adhered or secured to the neck of the patient, such as by a collar or cuff wrapped around the neck, by adhesive patches, or by a combination of these or by any other means. Collar 30 may further include an attaching device 40, such as hooks, loops, and/or fasteners, to attach a first end 12A of collar 30 with a second end 12B of collar 30 that is opposite to the first end 12A. In some examples, attaching device 40 may help provide improved comfortability around the cervical region. Second end 12B may further include a mating attaching device (not shown) to match with and attach to attaching device 40 to secure collar 30 around the neck of a patient. Sensor electrode array 26 may be positioned on collar 30 to be positioned generally along the laryngeal region and underneath the chin of a patient when collar 30 is wrapped around patient to sense activation of muscles controlled by laryngeal nerve.

In some examples, one or more of the electrodes in the first stimulating electrode array 22 may be raised or proud of the inner surface 60 of the collar 30 so that one or more of the electrodes in the first stimulating electrode array 22 may press into the neck to make better contact to increase conductivity when the collar 30 is wrapped around the neck. In some examples, one or more of the electrodes in the second stimulating electrode array 24 may be raised or proud of the inner surface 60 of the collar 30 so that one or more of the electrodes in the second stimulating electrode array 24 may press into the neck to make better contact to increase conductivity when the collar 30 is wrapped around the neck. In some examples, this configuration of one or more of the electrodes in a respective electrode array may lower impedance and may position the electrodes physically closer to a vagus nerve. In some examples, collar 30 may include an arc-shape 32 configured to be positioned under a chin of a patient when wrapped on a patient. The arc-shape 32 may be considered to be on a front-side of collar 30.

First stimulating electrode array 22 may positioned on collar 30 to be positioned generally over a left or right cervical vagus nerve when collar 30 is secured around a neck of a patient to provide VNS to the respective vagus nerve the first stimulating electrode array 22 is positioned over. Second stimulating electrode array 24 may positioned on collar 30 to be positioned generally over a cervical vagus nerve, opposite of the vagus nerve the first stimulating electrode array 22 is positioned generally over, when collar 30 is secured around a neck of a patient to provide VNS to the respective nerve the second stimulating electrode array 24 is positioned over. The positioning of the first stimulating electrode array 22 and the second stimulating electrode array 24 on collar 30 may provide a bilateral array of electrodes arranged over the left and right cervical vagus nerves to allow for unilateral, bilateral, or alternating-side stimulation of the vagus nerves of the patient. This may enable a particular type of stimulation therapy to be provided based on a therapy requirement of a patient. Additionally, the bilateral stimulation electrode arrays 22, 24 provide multiple potential stimulation zones, greatly increasing the chance of successful stimulation based on initial securement of collar 30 to patient and stimulation feedback.

In some examples, one or more sensors of sensor array 26 may be one or more of electromyography (EMG) sensors, e.g., electrodes, or accelerometers. One or more sensors of sensor array 26 may additionally or alternatively include one or more sensors to identify changes in electroencephalography (EEG), blood pressure, pulse, blood flow, respiration, temperature, activation of muscles not in the larynx, or any metrics indicative of VNS. Sensor array 26 may be configured to detect respective features indicative of muscle activation of a patient, such as laryngeal muscle activation of a patient. In some examples, when sensors of sensor array 26 are electrodes, there may be common arrays of electrodes that may selectively be used for delivering stimulation and sensing.

In an example in which sensors of sensor array 26 include one or more EMG sensors, EMG sensors may be configured to detect laryngeal muscle activation of a patient when collar 30 is secured on the patient. Sensor array 26 may positioned on collar 30 to be positioned generally over the larynx region of a patient when collar 30 is secured around a neck of a patient to detect laryngeal muscle activation. In some examples, EMG sensors may project from the inner surface 60 of collar 30, such that when the collar 30 is secured around the neck of a person receiving therapy, EMG sensors create more pressure/apposition against the skin of a patient. Detecting an amount of laryngeal muscle activity is above a laryngeal muscle activity threshold may indicate activation of the laryngeal nerve, which is an indication of VNS.

In an example in which sensors of sensor array 26 include one or more accelerometers, the accelerometers may be configured to monitor activation of laryngeal muscles and/or other muscles. For example, measurements by one or more accelerometers may indicate activity of laryngeal muscles above a laryngeal muscle threshold that indicates activation of muscles controlled by laryngeal nerve, which is an indication of VNS. In some examples, measurements by one or more accelerometers may indicate muscle movement that does not correspond to laryngeal muscle movement, which may indicate mispositioning of collar 30 on a patient.

In some examples, a drop in pulse, e.g., pulse rate, during stimulation therapy may indicate VNS. In some examples, one or more sensors of sensor array 26 may be configured to sense a pulse of a patient. In some examples, one or more of electrodes in the first stimulating electrode array 22 and/or second stimulating electrode array 24 may be configured to sense cardiac depolarizations indicative of a pulse of a patient. In some examples, one or more external sensors configured to communicate with collar 30 may be configured to sense a pulse of a patient. In some examples, one or more of sensors of sensor array 26, electrodes in the first stimulating electrode array 22 and/or second stimulating electrode array 24, and/or external sensors, such as electrocardiogram (ECG) leads of a device other than collar 30, configured to communicate with collar 30 may be configured to sense a pulse of a patient.

In some examples, controller 70 may determine a pulse drop based on the sensed pulse of the patient over a period of time during stimulation therapy. In some examples, controller 70 may determine whether the pulse drop during stimulation therapy satisfies a pulse drop VNS threshold that indicates VNS.

In some examples, a drop in blood pressure during stimulation therapy may indicate VNS. In some examples, one or more sensors of sensor array 26 may be configured to sense blood pressure of a patient. In some examples, one or more of electrodes in the first stimulating electrode array 22 and/or second stimulating electrode array 24 may be configured to sense blood pressure of a patient. In some examples, one or more external sensors configured to communicate with collar 30 may be configured to sense blood pressure of a patient. In some examples, one or more of sensors of sensor array 26, electrodes in the first stimulating electrode array 22 and/or second stimulating electrode array 24, and/or external sensors, such as an external cuff of a device other than collar 30, configured to communicate with collar 30 may be configured to sense blood pressure of a patient.

In some examples, controller 70 may determine a blood pressure drop based on the sensed blood pressure of the patient over a period of time during stimulation therapy. In some examples, controller 70 may determine whether the blood pressure drop during stimulation therapy satisfies a blood pressure drop VNS threshold that indicates VNS.

In some examples, controller 70 may determine whether one or more vagus nerves are being stimulated based on one or more of laryngeal muscle activity, pulse drop of the patient during stimulation therapy, and/or blood pressure drop during stimulation therapy. In some examples, controller 70 may generate an output to indicate whether one or more vagus nerves are being stimulated based on one or more of laryngeal muscle activity, pulse drop of the patient during stimulation therapy, and/or blood pressure drop during stimulation therapy.

A lining of inner surface 60 of collar 30 may be coated with a conductive gel to promote better electrical contact between the collar and the skin. Additionally, or alternatively, one or more of electrodes in the first stimulating electrode array 22 and/or second stimulating electrode array 24 and sensors in sensor array 26, may be coated with a conductive gel to promote better electrical contact between the collar and the skin. In some examples, collar 30 may be manufactured with such gel pre-applied to the collar, electrodes, and/or sensors. In some examples, the gel may be protected by a structure or film easily removable by a user, such as a caregiver, or may be automatically removed when stimulation device 10 is removed from its packaging.

In some examples, collar 30 may include a controller 70 electrically and/or communicatively coupled to one or more of first stimulating electrode array 22, second stimulating electrode array 24, or sensor array 26. While FIG. 1 shows collar 30 including controller 70, in some examples, controller 70 may be external to collar 30 and electrically and/or communicatively coupled to one or more of first stimulating electrode array 22, second stimulating electrode array 24, or sensor array 26.

Controller 70 may provide and/or adjust stimulation of one or more of the first stimulating electrode array 22 or second stimulating electrode array 24. In some examples, controller 70 may adjust the amplitude, pulse width, stimulation period, electrode current geometry, and/or waveform of the stimulation. For example, amplitude, pulse width, and/or waveform of the stimulation signal provided to one or more of the first stimulating electrode array 22 or second stimulating electrode array 24 may be varied or adjusted based on one or more of body type of patient or signal requirement to activate one or more vagus nerves. Controller 70 may adjust amplitude, pulse width, stimulation period, electrode current geometry, and/or waveform of the stimulation signal provided to one or more of the first stimulating electrode array 22 or second stimulating electrode array 24 based on changes in impedance. In some examples, controller 70 may adjust diploe patterns within first stimulating electrode array 22 and/or second stimulating electrode array 24. For example, controller 70 may pair different combinations of electrodes in a respective electrode array to create different dipoles, may create multiple diploes within an electrode array, and/or use one or more electrodes of a respective electrode array as a monopole. In some examples, controller 70 may provide a stimulation waveform that includes short bursts of high frequency stimulation, such as, but not limited to, 5 kilohertz (kHz) sine waves repeating blocks with a duration of 500 μsec that is repeated at a frequency of 25 Hertz (Hz). In some examples, a stimulation waveform may be monophasic or biphasic with amplitudes from 0-25 mA, a pulse width from 20-450 us and/or frequency from 5-500 Hz. Amplitudes, pulse width, and/or frequency may be amounts outside of these ranges as well. In some examples, controller 70 may be operable by a user, such as a clinician, EMT, or patient.

In some examples, controller 70 may be a computing device including one or more of processing circuitry, memory, sensing circuitry, stimulating circuitry, or communication circuitry. For example, an external computing device 90 may communicate with controller 70 via communication circuitry. In some examples, computing device 90 may include smartphones, desktop, laptop, or tablet computers, or workstations. Computing device 90 may include a mobile application to communicate with controller 70. The mobile application may include preset information pertaining to type of therapy, intensity, past treatments, patient history, etc. In one example, specific features on the application may also be unlocked by a manufacturer, supplier or healthcare provider based on pre-approved therapy for the patient. In some examples, controller 70 may receive information and/or instructions from computing device 90 pertaining to type of therapy, intensity, past treatments, patient history, etc. In some examples, some or all of processing discussed as being performed by controller 70, such as comparing, determining, adjusting, etc., may be performed by computing device 90 and communicated to controller 70 for data transfer.

Stimulation device 10 may include collar 30, first stimulating electrode array 22, second stimulating electrode array 24, and sensor array 26. Stimulation device 10 may further includer controller 70 or be communicatively coupled to controller 70. In some examples, when collar 30 is positioned on a patient to provide stimulation therapy to one or more vagus nerves of the patient, controller 70 may deliver stimulation therapy via first stimulating electrode array 22 and/or second stimulating electrode array 24 at an initial amount. In some examples, the initial amount of stimulation therapy may be predetermined. In some examples, the initial amount of stimulation therapy may be based on the patient, such as one or more of body type, type of health event occurring, age, weight, or other physiological data of patient. In some examples, the initial amount of stimulation therapy may be set by a user, such as a clinician or an EMT. Some examples of features of stimulation therapy to be provided via first stimulating electrode array 22 and/or second stimulating electrode array 24 may include an amplitude and/or waveform of the stimulation therapy. In some examples, an additional or alternative feature of stimulation therapy to be provided via first stimulating electrode array 22 and/or second stimulating electrode array 24 may include whether the stimulation is unilateral, bilateral, or alternating-side stimulation. There may be additional features of stimulation therapy to be provided via first stimulating electrode array 22 and/or second stimulating electrode array 24, such as pulse rate, duration, and/or other features for providing stimulation therapy.

Features of stimulation therapy to be provided may be determined for the initial amount of stimulation therapy to be provided via first stimulating electrode array 22 and/or second stimulating electrode array 24. Upon an initial amount of stimulation therapy being provided, sensor array 26 may detect activation of muscles controlled by laryngeal nerve. Controller 70 may compare the detected amount by sensor array 26 to an activation threshold. In response to the detected amount of laryngeal muscle activation being greater than or equal to an activation threshold, controller 70 determines one or more of the vagus nerves is stimulated. In response to the detected amount of laryngeal muscle activation being less than the activation threshold, controller 70 determines the vagus nerves were either not stimulated or not adequately stimulated.

In response to controller 70 determining the vagus nerves were either not stimulated or not adequately stimulated, controller 70 may generate an output to indicate the vagus nerves were either not stimulated or not adequately stimulated. In some examples, the output may be output via an output generator 95 coupled to collar 30. In some examples, the output generator 95 may be a light and the output may include an error signal being flashed via the light. In some examples, the output generator 95 may be a speaker and the output may be an audio signal being output via the speaker. In some examples, the output generator 95 may be a combination of a speaker and light and the output may be a combination of a light and audio signal. Output generator 95 may be located at any position on collar 30. In some examples, output generator 95 may be external to collar 30. As an example, the generated output may indicate to a user, such as an EMT, that collar 30 needs to be repositioned on the patient to provide improved vagus nerve stimulation via first stimulating electrode array 22 and/or second stimulating electrode array 24 and/or improve signal acquisition via sensor array 26. In some examples, the generated output may also indicate that features of the stimulation therapy via first stimulating electrode array 22 and/or second stimulating electrode array 24 need to be adjusted.

In some examples, controller 70 may send the generated output to computing device 90. The computing device 90 may then output an audio or light signal to indicate the vagus nerves were either not stimulated or not adequately stimulated. In some examples, controller 70 may send computing device 90 an indication of whether collar 30 needs to be adjusted and/or features of the stimulation therapy via first stimulating electrode array 22 and/or second stimulating electrode array 24 needs to be adjusted. In some examples, the indication may be shown on a user interface of computing device 90 to inform a user, such as an EMT, what adjustments to make to features of stimulation therapy to provide efficient and effective stimulation therapy to one or more vagus nerves of the patient. In some examples, controller 70 may output an indication suggesting one or more adjustments to make to stimulation therapy based on at least the detections by sensor array 26. Some examples of adjustments may include adjusting one or more of an amplitude, waveform, pulse rate, duration, and/or other features of the stimulation therapy provided via first stimulating electrode array 22 and/or second stimulating electrode array 24. In some examples, controller 70 may output an indication suggesting the stimulation therapy be unilateral, bilateral, or alternating-side stimulation.

In some examples, in response to controller 70 determining the vagus nerves were either not stimulated or not adequately stimulated, controller 70 may adjust one or more features of the stimulation therapy provided via first stimulating electrode array 22 and/or second stimulating electrode array 24. For example, controller 70 may activate different electrodes in the first stimulating electrode array 22 and/or second stimulating electrode array 24. In some examples, controller 70 may adjust an amplitude, waveform, pulse rate, duration, and/or other features of the stimulation therapy. In some examples, controller 70 may adjust the stimulation therapy to be unilateral, bilateral, or alternating-side stimulation. For example, if the initial stimulation was unilateral via first stimulating electrode array 22, controller may adjust the stimulation therapy to be bilateral stimulation, alternating-side stimulation, or unilateral stimulation via second stimulating electrode array 24. In some examples, a user, such as an EMT, may adjust a position of collar 30 on patient to provide better signal acquisition and/or improved comfortability for patient. Controller 70 may also adjust any combination of the features of the stimulation therapy. A closed-loop feedback VNS therapy may provide quicker, simpler, and more effective VNS therapy to patient, which may be especially important during a health event such as a stroke, TBI, or other detrimental conditions driven by inflammation.

After adjusting stimulation therapy, controller 70 may determine whether one or more vagus nerves are stimulated by the adjusted stimulation therapy based on one or more features detected by sensor array 26. For example, controller 70 may determine whether an amount of laryngeal muscle activity is above a laryngeal muscle activity threshold based on one or more features detected by sensor array 26. In some examples, if the controller 70 determines laryngeal muscle activity is below a laryngeal muscle activity threshold after one or more adjustments of features of stimulation therapy, controller may generate an output to indicate the vagus nerves were either not stimulated or not adequately stimulated in accordance with examples discussed above. In some examples, controller 70 may attempt multiple adjustments to features of stimulation therapy before generating an output to indicate the vagus nerves were either not stimulated or not adequately stimulated.

In some examples, collar 30 may include a power source 80, such as a battery. In some examples, collar 30 may include power source 80 and/or controller 70 electrically and/or communicatively coupled to one or more of first stimulating electrode array 22, second stimulating electrode array 24, or sensor array 26. In some examples, power source 80 may be external to collar 30 and collar 30 may be coupled to an external power source by a cable. In some examples controller 70 and power source 80 may be both be external to collar 30 and electrically coupled to electrodes and sensors in collar 30 with cables.

Figure 2A:
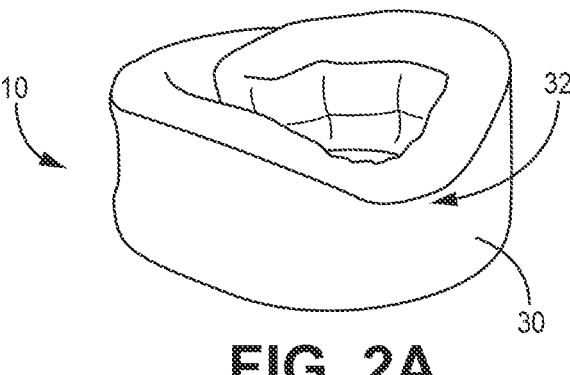
FIGS. 2A-2C illustrate a conceptual diagram of an example stimulation device in accordance with one or more techniques of the present disclosure.
Figure 2B:
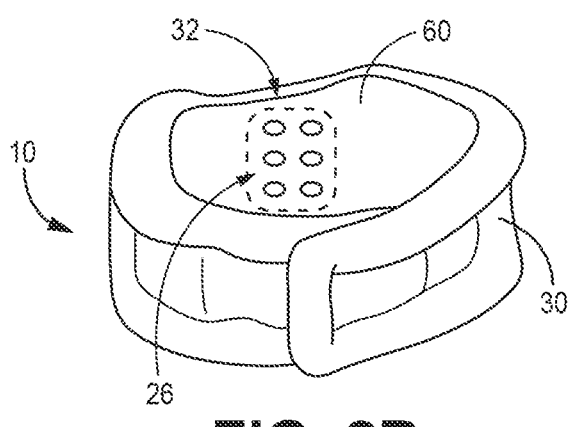
Figure 2C:
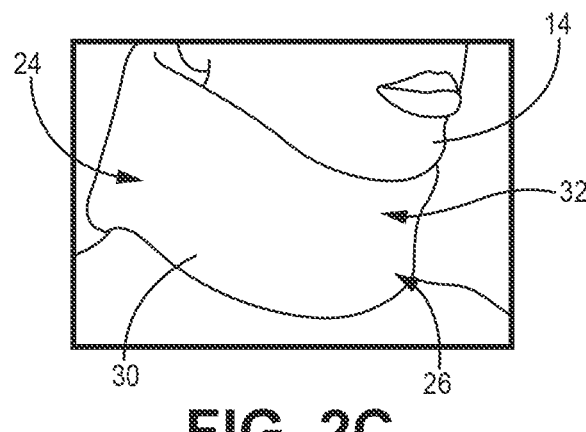

FIGS. 2A-2C illustrate a conceptual diagram of an example stimulation device 10 to be positioned on a patient 14. As shown in FIGS. 2A-2C, collar 30 may include an arc-shape 32 configured to be positioned under a chin of a patient when collar 30 is wrapped on patient 14. FIG. 2C shows an example of where sensor electrode array 26 may be positioned on collar 30 to be positioned generally along the laryngeal region and underneath the chin of patient 14 when collar 30 is wrapped around patient to sense activation of muscles controlled by laryngeal nerve. While FIG. 2C shows an example position of sensor electrode array 26, sensor electrode array 26 is positioned on an inner surface 60 of collar 30. FIG. 2C shows an example of where second stimulating electrode array 24 may be positioned on collar 30 to be positioned generally over a cervical vagus nerve when collar 30 is secured around a neck of patient 14 to provide VNS to the respective nerve the second stimulating electrode array 24 is positioned over. First stimulating electrode array 22 may be positioned on collar 30 to be positioned generally over a vagus nerve on a respective mirror opposite side of the neck of patient 14 that second stimulating electrode array 24 is positioned with respect to patient 14. While FIG. 2C shows an example position of second stimulating electrode array 24, second stimulating electrode array 24 is positioned on an inner surface 60 of collar 30. First stimulating electrode array 22 is also positioned on inner surface 60 of collar 30.

Figure 3A:
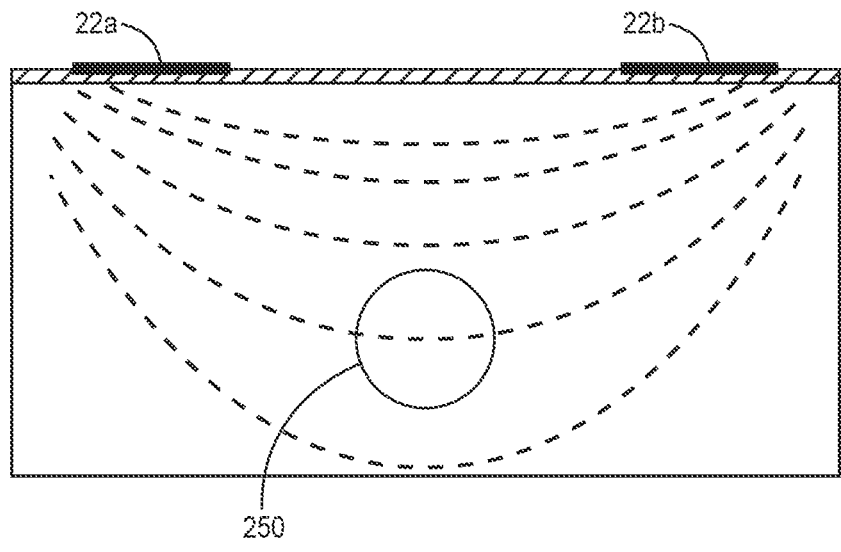
FIG. 3A-3C illustrate examples of stimulation of an example stimulating electrode array in accordance with one or more techniques of the present disclosure.
Figure 3B:
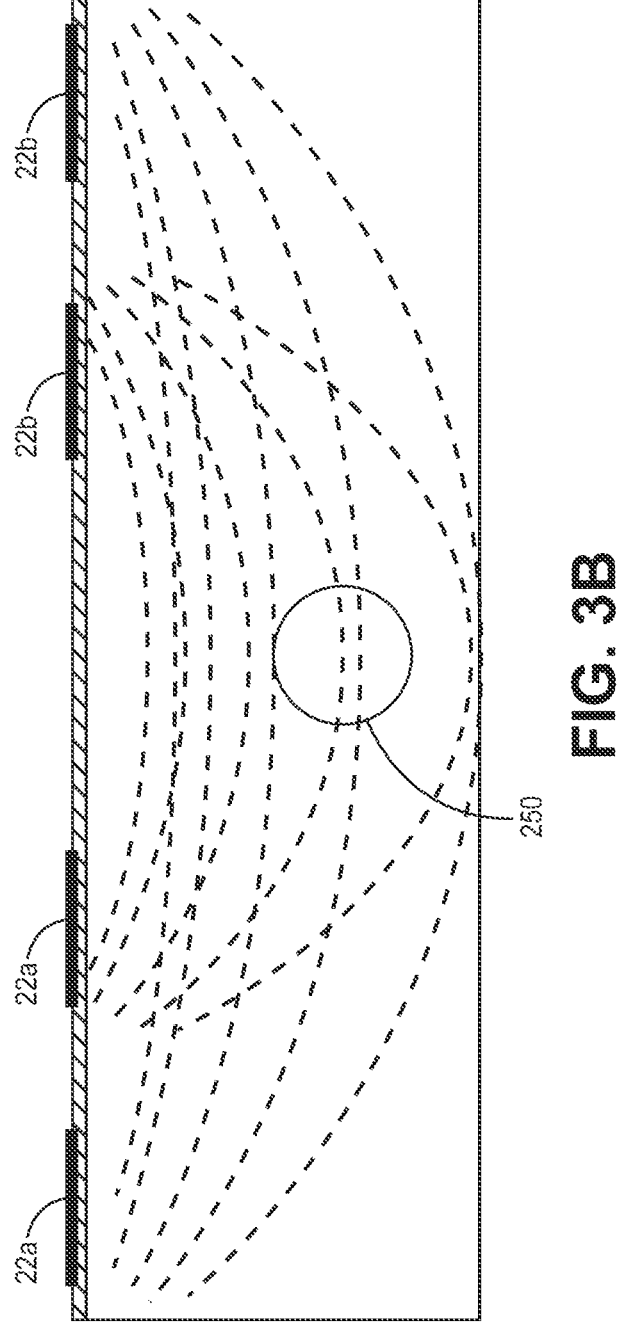
Figure 3C:
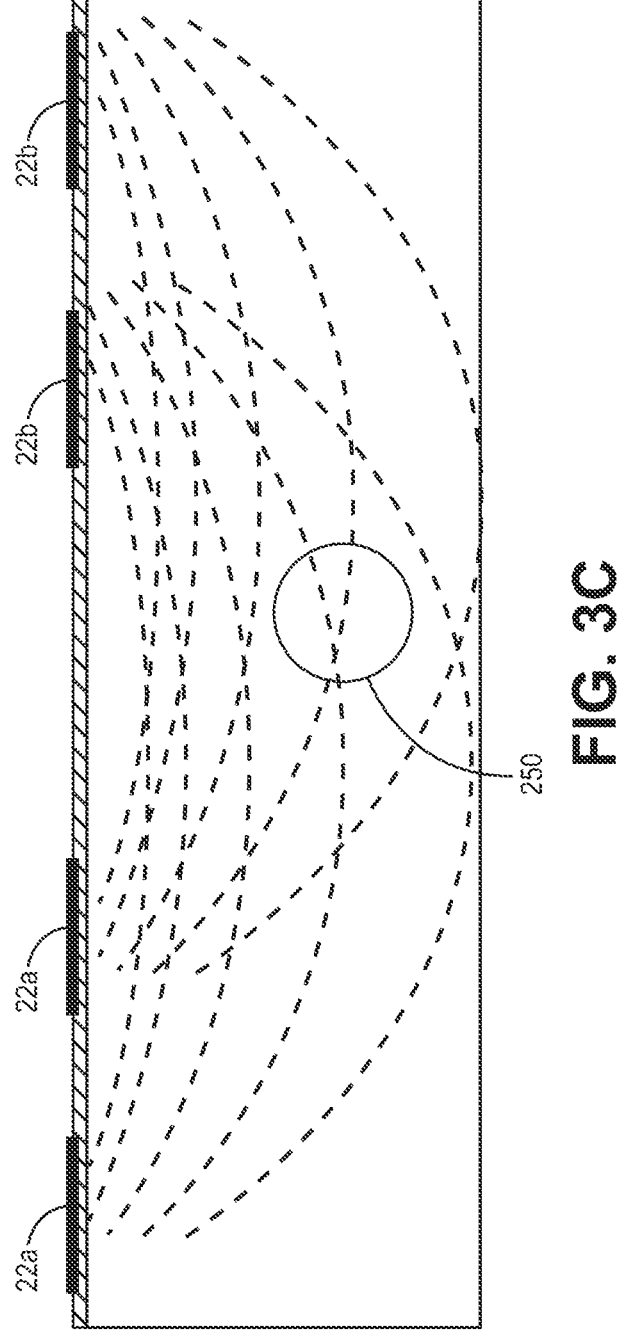

FIGS. 3A-3C illustrate examples of how electrodes of either first stimulating electrode array 22 and/or second stimulating electrode array 24 may be arranged and operated to deliver stimulation to a target nerve 250, in particular a vagus nerve. While the following discussion will refer to first stimulating electrode array 22 and electrodes 22a, 22b, . . . 22n in first stimulating electrode array 22, the description may also apply to second stimulating electrode array 24 and electrodes 24a, 24b, . . . 24n in second stimulating electrode array 24. In some examples, such as shown as an example in FIG. 3A, electrodes 22a and 22b may be positioned on opposite sides of target nerve 250 and may each create an electric field at the same frequency, for example 20 Hz, to deliver stimulation signals at an effective stimulation frequency.

In some examples, such as shown as an example in FIG. 3A, electrodes 22a and 22b may be positioned on opposite sides of target nerve 250 and may each create an electric field at the same frequency, for example 20 Hz, to deliver stimulation signals.

In some examples, such as shown as an example in FIGS. 3B, electrodes 22a and 22b may be positioned as nested electrode pairs on opposite sides of target nerve 250 and each electrode pair 22a and 22b may create two separate electrical fields at a high frequency, such as a carrier frequency. For example, electrode pair 22a may create two fields of frequencies of 3.000 kHz and 3.020 kHz and electrode pair 22b may create two fields of frequencies of 3.000 kHz and 3.020 kHz. Where the two fields overlap, the interfering fields would then have an effective stimulation frequency of 20 Hz.

In some examples, such as shown as an example in FIGS. 3C, electrodes 22a and 22b may be positioned as staggered electrode pairs on opposite sides of target nerve 250 and each electrode pair 22a and 22b may create two separate electrical fields at a high frequency, such as a carrier frequency. For example, electrode pair 22a may create two fields of frequencies of 3.000 kHz and 3.020 kHz and electrode pair 22b may create two fields of frequencies of 3.000 kHz and 3.020 kHz. Where the two fields overlap, the interfering fields would then have an effective stimulation frequency of 20 Hz.

While FIGS. 3A-3C showed two electrodes as an example, an array of electrodes, such as shown in FIG. 1 and described above, may be used to stimulate a target nerve. In addition, different configurations may be used to provide each field and in doing so, the peak interference may be steered and an optimal combination may be evaluated by monitoring the muscular contractions from the recurrent vagus nerve via sensor array 26.

Figure 4:
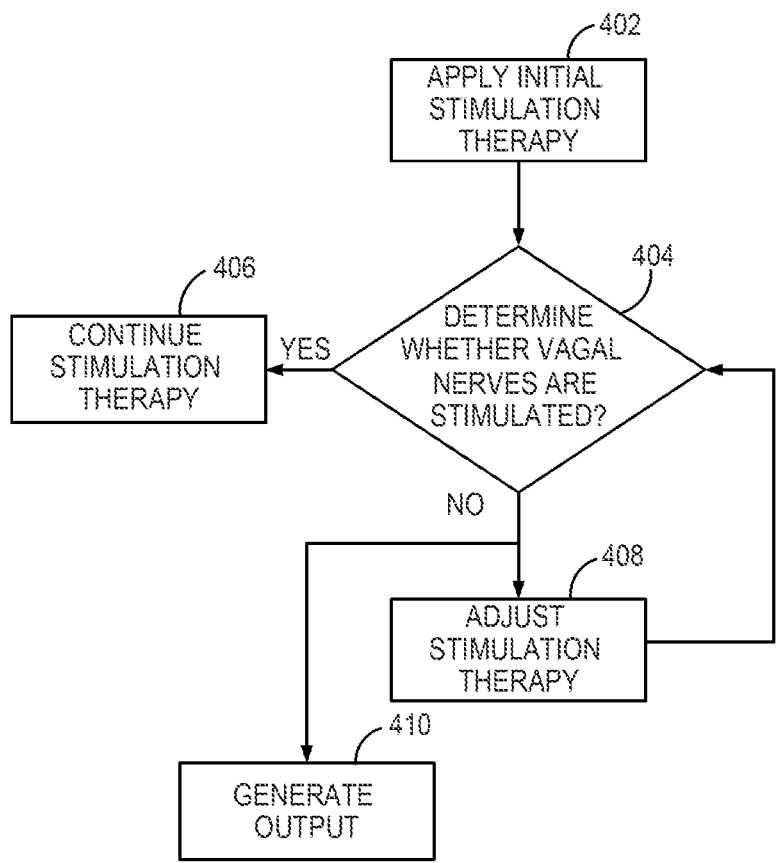
FIG. 4 is a flow diagram illustrating example techniques that may be performed by one or more of a system or device, in accordance with one or more techniques disclosed herein.

FIG. 4 is a flow diagram illustrating example techniques according to the present disclosure. Controller 70 may cause an initial stimulation therapy to be applied via one or more of first stimulating electrode array 22 or second stimulating electrode array 24 (402). Controller 70 may determine whether one or more vagus nerves are stimulated based on one or more features detected by sensor array 26 (404). For example, controller 70 may determine whether laryngeal muscle activation is greater than or equal to a laryngeal muscle activation threshold based on one or more features detected by sensor array 26 to determine whether vagus nerves are stimulated. In response to determining one or more vagus nerves are stimulated, controller 70 may continue causing the stimulation therapy to be delivered with same or similar features the stimulation therapy was being delivered (406). In response to determining one or more vagus nerves are not stimulated or not stimulated adequately, controller 70 may adjust one or more features of stimulation therapy to be applied via one or more of first stimulating electrode array 22 or second stimulating electrode array 24 (408). In response to determining one or more vagus nerves are not stimulated or not stimulated adequately, controller 70 may generate an output to indicate the vagus nerves are not stimulated or not stimulated adequately (410). In some examples, controller 70 may not generate an output until an amount of adjustments is greater than or equal to an adjustment threshold. For example, an adjustment threshold may be any amount between 1-10 adjustments. In some examples, an adjustment threshold may be greater than 10. In some examples, controller 70 may not generate an output until a time duration of applying and/or adjusting stimulation therapy is greater than or equal to a time duration threshold. For example, a time duration threshold may be anywhere between 1 seconds to 10 minutes. In some examples, a time duration threshold may be less than 1 second or greater than 10 minutes.

It should be noted that the techniques described herein, may not be limited to treatment or monitoring of a human patient. In alternative examples, the techniques of this disclosure may be applied to non-human patients, e.g., primates, canines, equines, pigs, sheep, and felines. These other animals may undergo clinical or research therapies that my benefit from the subject matter of this disclosure.

Various examples are discussed relative to one or more stimulation devices. It is recognized that the stimulation devices may include features and functionality in addition to electrical stimulation. Many of these additional features are expressly discus sed herein. A few example features include, but are not limited to, different types of sensing capabilities and different types of wireless communication capabilities. For ease of discussion, the present disclosure does not expressly recite every conceivable combination of the additional features, such as by repeating every feature each time different examples and uses of the stimulation devices are discussed.

The techniques of this disclosure may be implemented in a wide variety of computing devices, medical devices, or any combination thereof. Any of the described units, circuitry or components may be implemented together or separately as discrete but interoperable logic devices. Depiction of different features as circuitry or units is intended to highlight different functional aspects and does not necessarily imply that such circuitry or units must be realized by separate hardware or software components. Rather, functionality associated with one or more circuitry or units may be performed by separate hardware or software components, or integrated within common or separate hardware or software components.

The disclosure contemplates computer-readable storage media comprising instructions to cause a processor to perform any of the functions and techniques described herein. The computer-readable storage media may take the example form of any volatile, non-volatile, magnetic, optical, or electrical media, such as a RAM, ROM, NVRAM, EEPROM, or flash memory that is tangible. The computer-readable storage media may be referred to as non-transitory. A server, client computing device, or any other computing device may also contain a more portable removable memory type to enable easy data transfer or offline data analysis.

The techniques described in this disclosure, including those attributed to various circuitry and various constituent components, may be implemented, at least in part, in hardware, software, firmware or any combination thereof. For example, various aspects of the techniques may be implemented within one or more processors, including one or more microprocessors, DSPs, ASICs, FPGAs, or any other equivalent integrated, discrete logic circuitry, or other processing circuitry, as well as any combinations of such components, remote servers, remote client devices, or other devices. The term "processing circuitry" or "processing circuitry" may generally refer to any of the foregoing logic circuitry, alone or in combination with other logic circuitry, or any other equivalent circuitry.

Such hardware, software, firmware may be implemented within the same device or within separate devices to support the various operations and functions described in this disclosure. In addition, any of the described units, circuitry or components may be implemented together or separately as discrete but interoperable logic devices. Depiction of different features as circuitry or units is intended to highlight different functional aspects and does not necessarily imply that such circuitry or units must be realized by separate hardware or software components. Rather, functionality associated with one or more circuitry or units may be performed by separate hardware or software components, or integrated within common or separate hardware or software components. For example, any circuitry described herein may include electrical circuitry configured to perform the features attributed to that particular circuitry, such as fixed function processing circuitry, programmable processing circuitry, or combinations thereof.

In some examples, a computer-readable storage medium comprises non-transitory medium. The term "non-transitory" may indicate that the storage medium is not embodied in a carrier wave or a propagated signal. In certain examples, a non-transitory storage medium may store data that may, over time, change (e.g., in RAM or cache).

This disclosure includes the following non-limiting examples.

Example 1: A system includes a collar; a first stimulating electrode array positioned on the collar and configured to delivery stimulation therapy to a patient; a second stimulating electrode array being positioned on the collar and configured to deliver stimulation therapy to the patient; a sensor array being positioned on the collar and configured to detect one or more features indicative of laryngeal muscle activity of the patient; and a controller configured to control stimulation therapy to be delivered via the first stimulating electrode array and the second stimulating electrode array.

Example 2: The system of example 1, wherein the senor array is positioned on the collar between the first stimulating electrode array and the second stimulating electrode array when the collar is outstretched.

Example 3: The system of any of examples 1-2, wherein the collar includes a chin arc and the sensor array is positioned below the chin arc when the collar is positioned around a neck of the patient.

Example 4: The system of any of examples 1-3, wherein the first stimulating electrode array is positioned to deliver stimulation therapy to a left vagus nerve of the patient and the second stimulating electrode array is positioned to deliver stimulation therapy to a right vagus nerve of the patient when the collar is positioned around a neck of the patient.

Example 5: The system of any of examples 1-4, wherein the controller is further configured to control the stimulation therapy based on at least the detected features indicative of laryngeal muscle activity of the patient.

Example 6: The system of any of examples 1-5, wherein the controller is further configured to: determine a level of laryngeal muscle activity based on the detected features by the sensor array; determine the level of laryngeal muscle activity is less than a laryngeal muscle activity threshold; and in response to determining the level of laryngeal muscle activity is less than the laryngeal muscle activity threshold, adjust one or more features of the stimulation therapy to be delivered via one or more of the first stimulating electrode array or second stimulating electrode array.

Example 7: The system of any of examples 1-5, wherein the controller is further configured to: determine a level of laryngeal muscle activity based on the detected features by the sensor array; determine the level of laryngeal muscle activity is greater than or equal to a laryngeal muscle activity threshold; and in response to determining the level of laryngeal muscle activity is greater than or equal to the laryngeal muscle activity threshold, maintain features of the stimulation therapy to be delivered via one or more of the first stimulating electrode array or second stimulating electrode array.

Example 8: The system of any of examples 1-5, wherein the controller is further configured to: determine a level of laryngeal muscle activity based on the detected features by the sensor array; determine the level of laryngeal muscle activity is less than a laryngeal muscle activity threshold; and in response to determining the level of laryngeal muscle activity is less than the laryngeal muscle activity threshold, generate an output to indicate one or more vagus nerves are not being stimulated.

Example 9: The system of example 8, wherein the generated output includes suggested adjustments to make to a position of the collar on the patient or adjustments to one or more features of the stimulation therapy.

Example 10: The system of any of examples 8-9, wherein the generated output includes one or more of an audio or visual alarm signal.

Example 11: The system of any of examples 8-10, further including an output generator to output one or more of an audio or visual alarm signal.

Example 12: The system of any of examples 1-11, wherein the laryngeal muscle activity being greater than or equal to the laryngeal muscle activity threshold indicates vagus nerve stimulation.

Example 13: The system of any of examples 1-12, wherein the system is a stimulation device.

Example 14: The system of any of examples 1-13, wherein one or more sensors of the sensory array is an electromyography sensor.

Example 15: The system of any of examples 1-14, wherein one or more sensors of the sensory array is an accelerometer.

Example 16: A method includes applying, by a controller, initial stimulation therapy to a patient via one or more of a first stimulating electrode array and a second stimulating electrode array, the first stimulating electrode array and the second stimulating electrode array being positioned on a collar; detecting, by a sensor array, one or more features indicative of laryngeal muscle activity of the patient, the sensory array being positioned on the collar; determining, by the controller, a level of the laryngeal muscle activity based on the one or more features; and determining, by the controller, whether the level of the laryngeal muscle activity is less than a laryngeal muscle activity threshold.

Example 17: The method of example 16, further includes in response to determining the laryngeal muscle activity is less than the laryngeal muscle activity threshold, adjusting, by the controller, one or more features of the stimulation therapy to be applied via one or more of the first stimulating electrode array and the second stimulating electrode array.

Example 18: The method of any of examples 16-17, further includes in response to determining the laryngeal muscle activity is less than the laryngeal muscle activity threshold, outputting, by the controller, an indication that one or more vagus nerves are not being stimulated.

Example 19: The method of any of examples 16 through 18, further includes in response to determining the laryngeal muscle activity is greater than or equal to the laryngeal muscle activity threshold, maintaining features of the stimulation therapy to be applied via one or more of the first stimulating electrode array and the second stimulating electrode array.

Example 20: The method of any of examples 17 through 19, further includes applying, by the controller, the adjusted stimulation therapy to the patient via one or more of the first stimulating electrode array and the second stimulating electrode array; detecting, by the sensor array, one or more features indicative of laryngeal muscle activity of the patient while the adjusted stimulation therapy is being applied; determining, by the controller, a level of the laryngeal muscle activity based on the detected one or more features while the adjusted stimulation therapy is being applied; and determining, by the controller, whether the level of the laryngeal muscle activity while the adjusted stimulation therapy is being applied is less than a laryngeal muscle activity threshold.

Example 21: The method of example 20, further includes in response to determining the laryngeal muscle activity while the adjusted stimulation therapy is being applied is less than the laryngeal muscle activity threshold, adjusting, by the controller, one or more features of the adjusted stimulation therapy to be applied via one or more of the first stimulating electrode array and the second stimulating electrode array.

Example 22: The method of any of examples 20-21, further includes in response to determining the laryngeal muscle activity while the adjusted stimulation therapy is being applied is less than the laryngeal muscle activity threshold, outputting, by the controller, an indication that one or more vagus nerves are not being stimulated.

Example 24: A computer-readable medium storing instructions that when executed by one or more processors cause the one or more processors to perform the method of any of examples 1-23.

Various examples have been described herein. Any combination of the described operations or functions is contemplated. These and other examples are within the scope of the following claims. Based upon the above discussion and illustrations, it is recognized that various modifications and changes may be made to the disclosed examples in a manner that does not require strictly adherence to the examples and applications illustrated and described herein. Such modifications do not depart from the true spirit and scope of various aspects of the disclosure, including aspects set forth in the claims.

What is claimed is:

1. A system comprising:
a collar;
a first stimulating electrode array positioned on the collar and configured to deliver stimulation therapy to a patient;
a second stimulating electrode array being positioned on the collar and configured to deliver stimulation therapy to the patient;
a sensor array being positioned on the collar and configured to detect one or more features indicative of laryngeal muscle activity of the patient; and
a controller configured to control stimulation therapy to be delivered via the first stimulating electrode array and the second stimulating electrode array.

2. The system of claim 1, wherein the senor array is positioned on the collar between the first stimulating electrode array and the second stimulating electrode array when the collar is outstretched.

3. The system of claim 1, wherein the collar includes a chin arc and the sensor array is positioned below the chin arc when the collar is positioned around a neck of the patient.

4. The system of claim 1, wherein the first stimulating electrode array is positioned to deliver stimulation therapy to a left vagus nerve of the patient and the second stimulating electrode array is positioned to deliver stimulation therapy to a right vagus nerve of the patient when the collar is positioned around a neck of the patient.

5. The system of claim 1, wherein the controller is further configured to control the stimulation therapy based on at least the detected features indicative of laryngeal muscle activity of the patient.

6. The system of claim 1, wherein the controller is further configured to:
determine a level of laryngeal muscle activity based on the detected features by the sensor array;
determine the level of laryngeal muscle activity is less than a laryngeal muscle activity threshold; and
in response to determining the level of laryngeal muscle activity is less than the laryngeal muscle activity threshold, adjust one or more features of the stimulation therapy to be delivered via one or more of the first stimulating electrode array or second stimulating electrode array.

7. The system of claim 1, wherein the controller is further configured to:
determine a level of laryngeal muscle activity based on the detected features by the sensor array;
determine the level of laryngeal muscle activity is greater than or equal to a laryngeal muscle activity threshold; and
in response to determining the level of laryngeal muscle activity is greater than or equal to the laryngeal muscle activity threshold, maintain features of the stimulation therapy to be delivered via one or more of the first stimulating electrode array or second stimulating electrode array.

8. The system of claim 1, wherein the controller is further configured to:
determine a level of laryngeal muscle activity based on the detected features by the sensor array;
determine the level of laryngeal muscle activity is less than a laryngeal muscle activity threshold; and
in response to determining the level of laryngeal muscle activity is less than the laryngeal muscle activity threshold, generate an output to indicate one or more vagus nerves are not being stimulated.

9. The system of claim 8, wherein the generated output includes suggested adjustments to make to a position of the collar on the patient or adjustments to one or more features of the stimulation therapy.

10. The system of claim 8, wherein the generated output includes one or more of an audio or visual alarm signal.

11. The system of claim 8, further including an output generator to output one or more of an audio or visual alarm signal.

12. The system of claim 1, wherein the laryngeal muscle activity being greater than or equal to a laryngeal muscle activity threshold indicates vagus nerve stimulation.

13. The system of claim 1, wherein the system is a stimulation device.

14. The system of claim 1, wherein one or more sensors of the sensory array is an electromyography sensor.

15. The system of claim 14, wherein one or more sensors of the sensory array is an accelerometer.

16. A method comprising:

applying, by a controller, initial stimulation therapy to a patient via one or more of a first stimulating electrode array and a second stimulating electrode array, the first stimulating electrode array and the second stimulating electrode array being positioned on a collar;

detecting, by a sensor array, one or more features indicative of laryngeal muscle activity of the patient, the sensory array being positioned on the collar;

determining, by the controller, a level of the laryngeal muscle activity based on the one or more features; and determining, by the controller, whether the level of the laryngeal muscle activity is less than a laryngeal muscle activity threshold.

17. The method of claim 16, further comprising:

in response to determining the laryngeal muscle activity is less than the laryngeal muscle activity threshold, adjusting, by the controller, one or more features of the stimulation therapy to be applied via one or more of the first stimulating electrode array and the second stimulating electrode array.

18. The method of claim 16, further comprising:

in response to determining the laryngeal muscle activity is less than the laryngeal muscle activity threshold, outputting, by the controller, an indication that one or more vagus nerves are not being stimulated.

19. The method of claim 16, further comprising:

in response to determining the laryngeal muscle activity is greater than or equal to the laryngeal muscle activity threshold, maintaining features of the stimulation therapy to be applied via one or more of the first stimulating electrode array and the second stimulating electrode array.

20. The method of claim 17, further comprising:

applying, by the controller, the adjusted stimulation therapy to the patient via one or more of the first stimulating electrode array and the second stimulating electrode array;

detecting, by the sensor array, one or more features indicative of laryngeal muscle activity of the patient while the adjusted stimulation therapy is being applied;

determining, by the controller, a level of the laryngeal muscle activity based on the detected one or more features while the adjusted stimulation therapy is being applied; and determining, by the controller, whether the level of the laryngeal muscle activity while the adjusted stimulation therapy is being applied is less than a laryngeal muscle activity threshold.

21. The method of claim 20, further comprising:

in response to determining the laryngeal muscle activity while the adjusted stimulation therapy is being applied is less than the laryngeal muscle activity threshold, adjusting, by the controller, one or more features of the adjusted stimulation therapy to be applied via one or more of the first stimulating electrode array and the second stimulating electrode array.

22. The method of claim 20, further comprising:

in response to determining the laryngeal muscle activity while the adjusted stimulation therapy is being applied is less than the laryngeal muscle activity threshold, outputting, by the controller, an indication that one or more vagus nerves are not being stimulated.

23. A non-transitory computer-readable medium storing instructions that when executed by one or more processors cause the one or more processors to perform:

applying initial stimulation therapy to a patient via one or more of a first stimulating electrode array and a second stimulating electrode array, the first stimulating electrode array and the second stimulating electrode array being positioned on a collar;

detecting, via a sensor array, one or more features indicative of laryngeal muscle activity of the patient, the sensory array being positioned on the collar;

determining level of the laryngeal muscle activity based on the one or more features; and determining whether the level of the laryngeal muscle activity is less than a laryngeal muscle activity threshold.

* * * * *